US008932253B2

(12) United States Patent
Gibson et al.

(10) Patent No.: US 8,932,253 B2
(45) Date of Patent: Jan. 13, 2015

(54) MEDICATION INFUSION DEVICE USING NEGATIVELY BIASED AMBIENT PRESSURE MEDICATION CHAMBER

(75) Inventors: Scott R. Gibson, Granada Hills, CA (US); Peter C. Lord, Valencia, CA (US)

(73) Assignee: Medallion Therapeutics, Inc., Valencia, CA (US)

( * ) Notice: Subject to any disclaimer, the term of this patent is extended or adjusted under 35 U.S.C. 154(b) by 507 days.

(21) Appl. No.: 13/287,651

(22) Filed: Nov. 2, 2011

(65) Prior Publication Data

US 2012/0130353 A1    May 24, 2012

Related U.S. Application Data

(63) Continuation of application No. 11/294,973, filed on Dec. 6, 2005, now Pat. No. 8,070,745, which is a continuation of application No. PCT/US2004/020117, filed on Jun. 23, 2004.

(60) Provisional application No. 60/483,015, filed on Jun. 25, 2003.

(51) Int. Cl.
| *A61M 37/00* | (2006.01) |
| *A61M 31/00* | (2006.01) |
| *A61K 9/22* | (2006.01) |
| *A61M 5/142* | (2006.01) |
| *A61M 5/145* | (2006.01) |

(52) U.S. Cl.
CPC ....... *A61M 5/14276* (2013.01); *A61M 5/14586* (2013.01); *A61M 2005/14264* (2013.01); *A61M 2205/0266* (2013.01)
USPC ..................... 604/132; 604/93.01; 604/891.1

(58) Field of Classification Search
USPC ......... 604/891.1, 892.2, 151, 131–134, 93.01
See application file for complete search history.

(56) References Cited

U.S. PATENT DOCUMENTS

| 3,831,203 A | * | 8/1974 | Ridgway ....................... 623/3.23 |
| 4,265,241 A | | 5/1981 | Portner et al. |
| 4,360,019 A | | 11/1982 | Portner et al. |
| 4,511,355 A | | 4/1985 | Franetzki et al. |
| 4,573,994 A | | 3/1986 | Fischell et al. |
| 4,661,097 A | * | 4/1987 | Fischell et al. ................ 604/123 |
| 4,714,462 A | | 12/1987 | DiDomenico |
| 4,718,893 A | | 1/1988 | Dorman et al. |
| 4,772,263 A | | 9/1988 | Dorman et al. |
| 4,781,689 A | | 11/1988 | Sealfon et al. |
| 4,838,887 A | | 6/1989 | Idriss |

(Continued)

FOREIGN PATENT DOCUMENTS

| WO | WO 03022338 A1 | 3/2003 |
| WO | WO 03099351 A2 | 12/2003 |

*Primary Examiner* — Rebecca E Eisenberg
(74) *Attorney, Agent, or Firm* — Henricks, Slavin & Holmes LLP

(57) ABSTRACT

A method and apparatus for infusing medication into a patient's body using a medication chamber referenced to ambient pressure. The apparatus includes a medication chamber enclosed by a peripheral wall which includes a movable portion configured to transfer exterior ambient pressure into the chamber. Means are provided for exerting a negative bias force acting on the movable portion in a direction opposed to the ambient pressure force. Thus, the resultant pressure in the chamber will be negative with respect to ambient pressure, reducing the risk that the chamber can be overpressurized and produce an unintended medication discharge.

15 Claims, 4 Drawing Sheets

(56) References Cited

U.S. PATENT DOCUMENTS

| | | |
|---|---|---|
| 5,045,064 A | 9/1991 | Idriss |
| 5,176,641 A | 1/1993 | Idriss |
| 5,281,210 A | 1/1994 | Burke et al. |
| 5,306,257 A | 4/1994 | Zdeb |
| 5,334,197 A * | 8/1994 | Kriesel et al. ........... 604/132 |
| 5,492,533 A | 2/1996 | Kriesel |
| 5,665,070 A | 9/1997 | McPhee |
| 5,707,361 A | 1/1998 | Slettenmark |
| 6,216,916 B1 | 4/2001 | Maddox et al. |
| 6,283,943 B1 | 9/2001 | Dy et al. |
| 6,394,981 B2 | 5/2002 | Heruth |
| 6,520,936 B1 | 2/2003 | Mann |
| 8,070,745 B2 | 12/2011 | Gibson et al. |
| 2001/0056259 A1 | 12/2001 | Skinkle et al. |
| 2002/0087147 A1 | 7/2002 | Hooper et al. |
| 2003/0198558 A1 | 10/2003 | Nason et al. |
| 2005/0087555 A1 | 4/2005 | Hatton et al. |

* cited by examiner

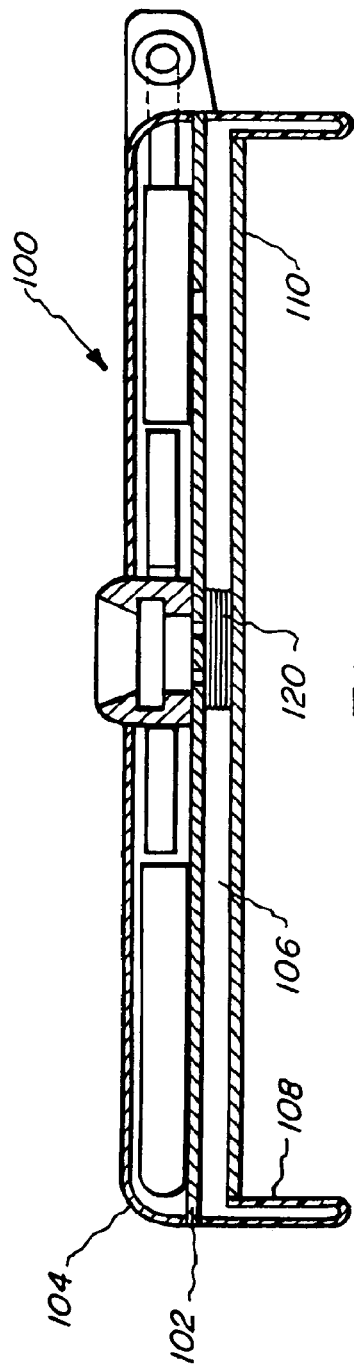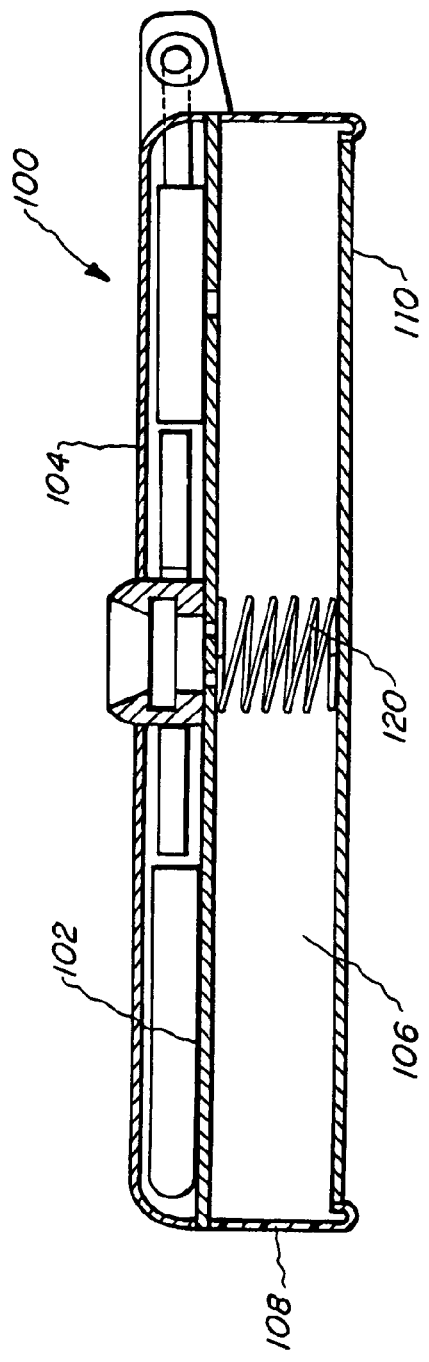

MEDICATION INFUSION DEVICE USING NEGATIVELY BIASED AMBIENT PRESSURE MEDICATION CHAMBER

RELATED APPLICATIONS

This application is a continuation of U.S. application Ser. No. 11/294,973, filed Dec. 6, 2005, now U.S. Pat. No. 8,070,745, which is a continuation of PCT Application Serial No. PCT/US2004/020117, filed Jun. 23, 2004, which claims priority to U.S. Provisional Application Ser. No. 60/483,015, filed Jun. 25, 2003.

FIELD OF THE INVENTION

This invention relates generally to medication infusion devices which include a chamber for storing fluid medication and means for extracting medication from the chamber for delivery to a patient's body site.

BACKGROUND OF THE INVENTION

Various types of implantable and/or external medication infusion devices are described in the literature. For example only, see U.S. Pat. Nos. 4,772,263 and 6,283,943 and the references cited therein which relate primarily to implantable devices. Many such devices employ a medication chamber together with a propellant reservoir which functions to isolate the chamber from changes in ambient pressure attributable, for example, to changes in altitude. More particularly, a typical propellant reservoir contains a biphasic propellant balanced between gas and liquid phases to maintain a constant pressure regardless of changes in reservoir volume. The pressure in the medication chamber is typically referenced (either positive or negative) to the constant reservoir pressure. Positive referenced devices have the advantage that the propellant can be selected to provide a constant driving pressure under defined operating conditions (e.g., constant flow applications) acting in a direction to force medication out of the chamber. Alternatively, negative referenced devices have inherent safety advantages; e.g., when refilling the chamber with a hypodermic needle, medication can be drawn into the chamber without the application of manual pressure to the needle. This assures that the needle will not discharge medication unless it has been properly placed in a device fill port and reduces the possibility of chamber overpressurization. Also, during normal operation, since chamber pressure is lower than ambient pressure, the pressure differential acts in a direction to draw fluid from the outlet catheter toward the chamber thus tending to reduce the risk of medication leakage into the patient's body.

Although the use of a propellant reservoir has the advantage of isolating the medication chamber from changes in ambient pressure, it nevertheless adds to device size, complexity, and cost. Accordingly, it has been recognized that, in some situations, it may be preferable to reference the medication chamber directly to ambient pressure. For example, U.S. Pat. No. 4,772,263 describes an infusion pump which includes a spring for producing a positive force on the drug chamber to force the solution therefrom.

SUMMARY OF THE INVENTION

The present invention is directed to a method and apparatus for infusing medication into a patient's body using a medication chamber referenced to ambient pressure (so as to avoid the need for, and attendant complexity of, a propellant reservoir) while achieving the safety and reliability of negative referenced propellant reservoir designs. Embodiments of the invention can be configured for use either exterior to a patient's body or implanted within a patient's body An apparatus in accordance with the invention includes a medication chamber enclosed by a peripheral (or boundary) member which includes a movable portion configured to transfer exterior ambient pressure into the chamber. Means are provided in accordance with the invention for exerting a negative bias force acting on the movable portion in a direction opposed to the force produced by the ambient pressure. Thus, the resultant pressure in the chamber will always be negative with respect to ambient pressure, reducing the risk that the chamber can be overpressurized and produce an unintended medication discharge.

The peripheral member defining the chamber can be variously formed in accordance with the invention. For example, the peripheral member (or wall) can be comprised of one or more rigid and/or flexible wall portions which cooperate to fully enclose the chamber. At least one wall portion is movable and has an exterior surface exposed to ambient pressure.

In one preferred embodiment, the peripheral member is defined by a rigid wall portion and a flexible wall portion, e.g., a resilient membrane, secured around its edge to the rigid wall portion to enclose the chamber therebetween. The exterior surface of the flexible wall portion is exposed to ambient pressure and a negative bias force is applied to the flexible wall portion acting in opposition to the ambient pressure. The negative bias force can be provided by various types of force generators, e.g., a magnet, the inherent resiliency of a properly configured resilient membrane, or by a spring member (e.g., leaf, coil, bellows, elastomeric material, etc). In any event, the bias force acts to create a pressure in the chamber which is negative with reference to ambient.

In accordance with the invention, medication is extracted from the negatively biased chamber by a selectively actuatable outlet pump.

In one alternative preferred embodiment, the chamber peripheral wall member can be comprised of first and second rigid wall portions connected by a flexible wall portion, e.g., a flexible shroud or bellows, which permits the rigid wall portions to move toward and away from one another to vary the chamber volume therebetween.

In a still further preferred embodiment, the chamber peripheral wall can be formed by the interior wall surface of a hollow cylinder and by a piston mounted for reciprocal linear movement in the cylindrical volume.

Regardless of the particular implementation of the chamber peripheral wall, embodiments of the invention are characterized by a movable wall portion which is exposed to ambient pressure and a bias force acting in opposition to the ambient pressure to produce a resultant chamber pressure which is negative with respect to the ambient pressure. The chamber peripheral wall, including the moveable wall portion, preferably has a geometry which optimizes volumetric efficiency, i.e., maximizes the useable volume and minimizes dead space volume or ullage. The bias force can be produced by a variety of force members including, for example, discrete springs of various types, elastomeric material, magnets, etc.

BRIEF DESCRIPTION OF THE FIGURES

FIGS. 4A and 4B schematically depict an alternative embodiment of the invention using a spring to provide the bias and respectively showing the movable wall portion in its compressed and extended positions;

DETAILED DESCRIPTION

Figure 2:
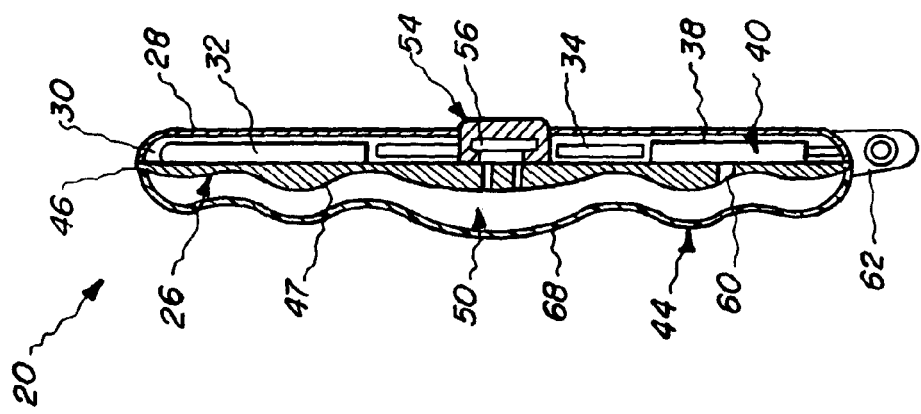
FIG. 2 is a schematic sectional view through the device of FIG. 1 showing the movable portion (e.g., resilient membrane) of the chamber peripheral (or boundary) wall in a fully extended (i.e., chamber full) position.
Figure 1:
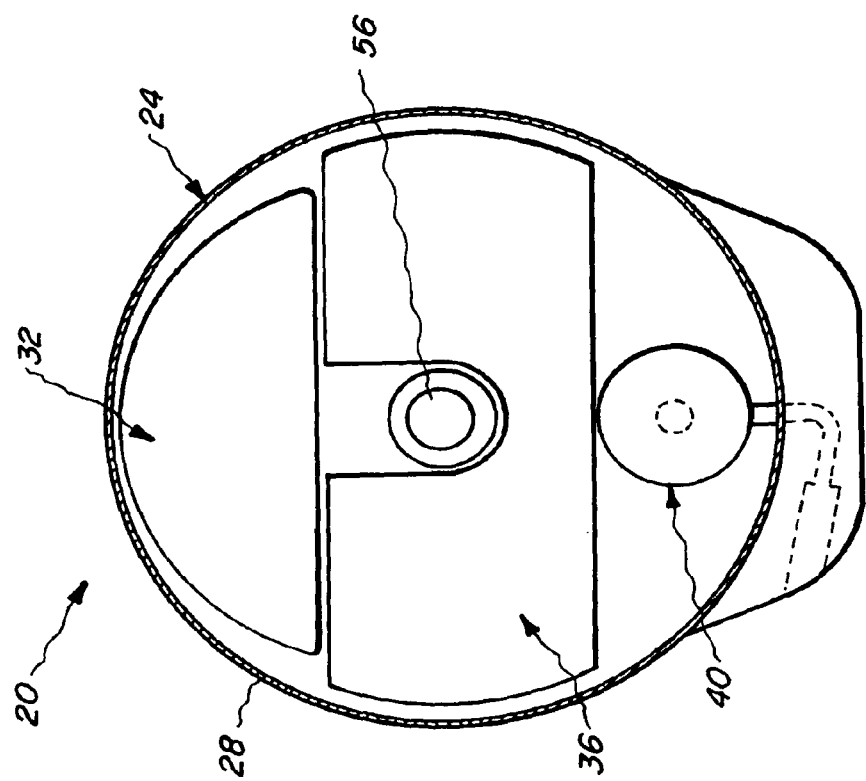
FIG. 1 is a schematic plan view of a preferred medication infusion device in accordance with the invention.

Attention is now directed to FIGS. 1 and 2 which illustrate a preferred embodiment of a medication device 20 in accordance with the present invention for controllably delivering medication to a patients body site. Although the particular device 20 illustrated in FIGS. 1 and 2 is intended for implanting in a patient's body, it should be understood that the invention also finds utility in applications where the device is carried externally.

As depicted in FIGS. 1 and 2, the device 20 is comprised of a housing 24 including a base plate 26 and a cover 28 supported on the base plate 26. The base plate 26 and cover 28 define one or more compartments therebetween, e.g., compartments 30, 34, 38 for housing various components such as battery 32, an electronics module 36, and an active medication pump 40.

FIG. 2 depicts a flexible and resilient membrane 44 secured along its edge 46 to the underside of the base plate 26. As will be explained in greater detail hereinafter, the membrane 44 is configured to naturally expand to the fully extended position shown in FIG. 2 to maximize the space, i.e., volume, of the closed medication chamber 50 formed between the membrane 44 and base plate surface 47. When the content of chamber 50 is evacuated, the ambient pressure acting against the membrane 44 will collapse it against base plate surface 47.

An inlet valve 54 is supported by the cover 28 and base plate 26 and affords communication to the interior of chamber 50. The inlet valve 54 can be conventionally constructed comprising a self healing septum 56 through which a hypodermic needle can be inserted to discharge medication into the chamber 50. As will be discussed hereinafter, inasmuch as the medication chamber 50, in accordance with the present invention, is maintained at a negative pressure relative to ambient pressure, the hypodermic needle, when properly inserted through septum 56, is able to discharge medication into the chamber 50 without the application of manual pressure to the hypodermic needle.

The active pump 40 has an inlet 60 which communicates with the chamber 50 for extracting medication therefrom. The pump 40 is coupled to a catheter outlet connector 62 through which medication is pumped for distribution to a body site.

In accordance with the present invention, the membrane 44 comprises a movable portion of a peripheral member or wall which defines and encloses the medication chamber 50. The exterior surface 68 of the membrane 44 is configured to be exposed to ambient pressure, i.e., that is the internal body pressure when the implantable device 20 is in situ. Typically, this ambient pressure will be very close to atmospheric pressure, which of course is dependent upon altitude, temperature, etc. The ambient pressure acts in a direction tending to compress the membrane 44 against the base plate 26. More particularly, when the chamber 50 is filled with medication, the membrane 44 will expand to its natural fully extended position shown in FIG. 2. However, when the medication is evacuated by action of pump 40, then the ambient pressure acts to collapse the membrane 44 toward the base plate surface 47.

In accordance with the present invention, a spring bias force is applied to the chamber movable wall portion, i.e., membrane 44 in FIG. 2, which acts in a direction to oppose the ambient pressure force so as to create a residual pressure in the chamber which is negative with reference to ambient.

Figure 3:
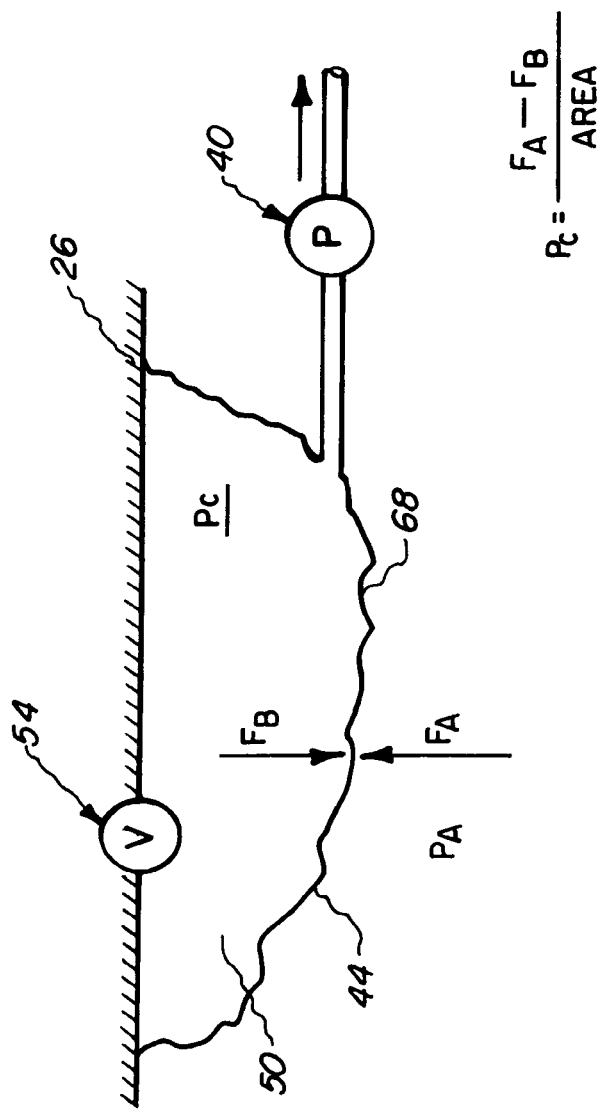
FIG. 3 is a schematic representation of the movable chamber wall portion depicting the application of ambient and bias forces to the wall portion in accordance with the invention.

More particularly, with reference to FIG. 3, note that the ambient pressure $P_A$ acting on the exterior surface 68 of movable wall portion 44 produces a force $F_A$ tending to move the wall portion 44 toward the base plate 26, i.e., to collapse the chamber 50. In accordance with the present invention, a bias force $F_B$ is created which acts in opposition to the force $F_A$. As shown, the chamber pressure $P_C$ will be negative with respect to the ambient pressure $P_A$ attributable to the negative bias force $F_B$.

The force $F_B$ can be provided in a variety of different ways. For example, the membrane 44 of FIG. 2 can comprise a part formed of metal or plastic material (e.g., nitinol, titanium, stainless steel, super alloys, composite material) configured so that in its natural or quiescent state it resiliently expands to the extended position represented in FIGS. 2 and 3. Thus, as the ambient pressure bears against, the movable wall portion of membrane 44 tending to move it toward its compressed position, it will develop a restoration force $F_B$ acting to oppose the compression. As an alternative to configuring wall portion 44 to inherently exhibit the desired resilient characteristic, a separate force generator, e.g., a spring, a magnet, a frictional member, etc. can be incorporated into the device structure.

Attention is now directed to FIG. 4A which depicts an alternative embodiment 100. The embodiment 100 includes a base plate 102 and cover 104 which can be considered identical to the corresponding components 26 and 28 discussed in connection with FIG. 2. The plate 102 defines a substantially rigid portion of a peripheral wall extending around and enclosing a medication chamber 106. The chamber peripheral wall, in accordance with the present invention, also includes a movable portion which in embodiment 100 comprises a flexible boot or shroud 108. The boot 108 carries a rigid wall portion 110 which is spaced from and oriented substantially parallel to plate 102. Thus, the chamber 106 in embodiment 100 is defined by the inner surfaces of wall portions 102 and 110 and flexible wall portion or boot 108.

In the embodiment 100, a force generator, or member, comprises a coil spring 120 mounted between the inner surfaces of wall portions 102 and 110. The spring member 120 is shown as a coil spring which is configured so that in its natural or quiescent state, e.g., in a vacuum, it is extended to the position shown in FIG. 4B. Ambient pressure acting on the outer surface of movable portion 110 acts in the direction to compress spring member 120 with the spring member thus providing a restoration or bias force acting in opposition to the force of the ambient pressure. Thus, the pressure within the chamber 106 will be maintained below the ambient pressure as a consequence of the force produced by spring 120 as was discussed in connection with FIG. 3. Typically, this spring force is selected to produce a chamber pressure which is negative with respect to ambient pressure by a differential within the range 0.1 to 5.0 psig.

Figure 5:
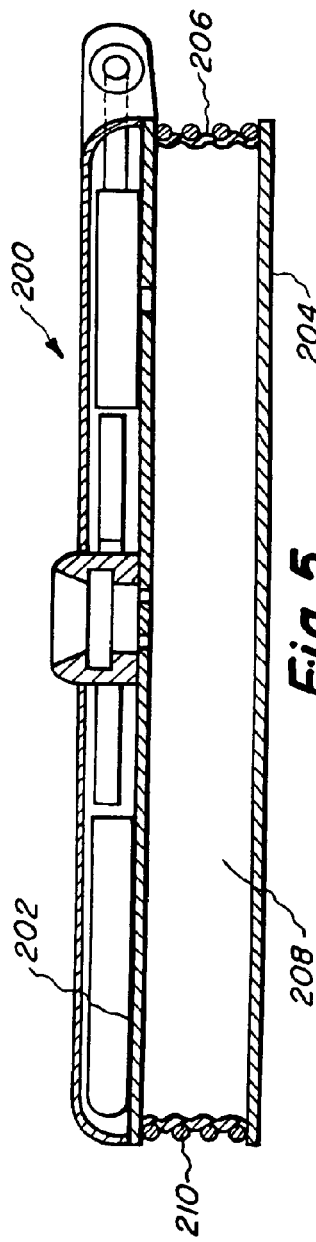
FIG. 5 is a schematic illustration of a further alternative embodiment of the invention using a bellows or exterior spring to provide the bias force.

FIG. 5 depicts a further alternative embodiment 200 in which the inner surfaces of a base plate 202, a movable rigid portion 204, and a flexible shroud or bellows 206 define and enclose a medication chamber 208. A coil spring 210 is depicted as being formed around the exterior of the shroud 206. The shroud 206 and coil spring 210 be formed separately or alternatively can be formed as an integral bellows member.

The embodiment of FIG. 5 operates identically to the embodiment of FIGS. 4A and 4B in that the spring 210 produces a bias force opposing the force of the ambient pressure bearing on wall portion 204. As medication is drawn from the chamber 208 by action of the active pump, the ambient pressure will displace wall portion 204 toward support plate 202 acting against the bias force provided by spring 210.

Figure 6:
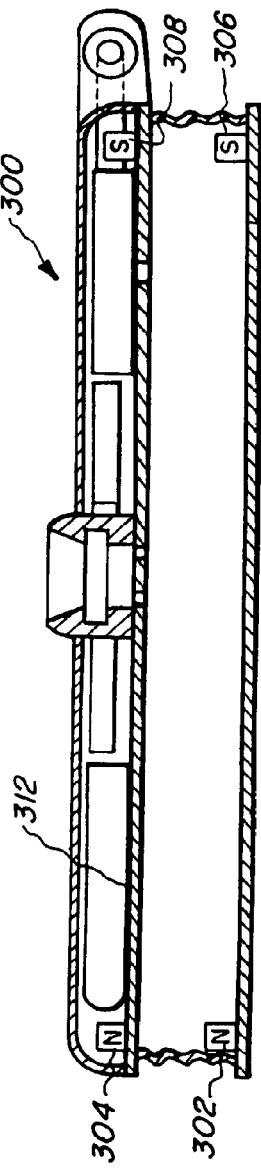
FIG. 6 is a schematic illustration of a still further alternative embodiment using magnetic repulsion to provide the bias force.

FIG. 6 illustrates an embodiment 300 which is similar in construction to the embodiment 200 in FIG. 5. However, in lieu of using a spring member to provide the negative bias force, the embodiment 300 uses magnetic repulsion to develop the negative bias force. More particularly, note in FIG. 6 that adjacent magnets 302 and 304 are similarly poled. Also note that adjacent magnets 306 and 308 are similarly poled. Thus, as the force produced by ambient pressure on the exterior surface of wall portion 310 acts to displace wall portion 310 toward base plate 312, the repulsion force produced by the magnets will increase in opposition to the ambient force. Of course, as has been discussed in connection with the earlier embodiments, this negative bias force will produce a chamber pressure which is negative with respect to the ambient pressure.

Figure 7:
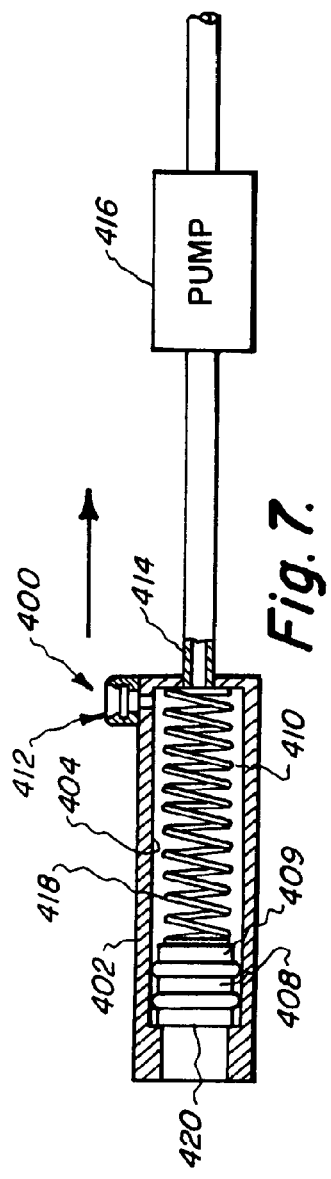
FIG. 7 is a schematic illustration of a still further embodiment using a hollow cylinder and a movable piston to define the chamber.

FIG. 7 depicts a still further embodiment 400. In the embodiment of FIG. 7, a hollow cylinder 402 is provided defining an interior wall surface 404. A piston 408 is mounted for reciprocal linear motion within the cylindrical volume defined by the interior wall surface 404. The piston 408 interior surface 409, together with wall surface 404, defines a medication chamber 410. An inlet valve 412 opens to the medication chamber and an outlet 414 couples the chamber 410 to an actuatable pump 416. A force generator, e.g., spring member 418, is shown mounted in the chamber 410 bearing against piston interior surface 409. The piston outer surface 420 is exposed to ambient pressure.

FIG. 7 depicts spring 418 in its expanded state with the chamber 410 filled with medication supplied via inlet valve 412. As medication is extracted from the chamber 410 by action of the pump 416, ambient pressure acting on the piston outer surface 420 will act to move the piston 408 along the interior wall surface 404 to compress spring 418 and diminish the volume of chamber 410. This action will be opposed by the restoration force of spring member 418 thus producing a pressure in chamber 410 which is negative with respect to the ambient pressure applied to the piston surface 420.

From the foregoing, it should now be appreciated that multiple exemplary embodiments have been described herein characterized by a chamber peripheral wall portion which is exposed to ambient pressure together with means for producing a bias force acting in opposition to the ambient pressure to produce a pressure within the chamber which is negative with respect to the ambient pressure. Although only a limited number of embodiments have been specifically described, it should be recognized by those skilled in the art that the invention can be implemented by a variety of alternative, essentially equivalent, structures conforming to the spirit of the invention and within the intended scope of the appended claims.

The invention claimed is:

1. A method, comprising the steps of:
   biasing a movable wall member, which is carried by a pump housing and has a first side that defines a fluid chamber and a second side that is exposed to ambient pressure, away from the pump housing with enough force to create a pressure within the fluid chamber that is negative with respect to the ambient pressure; and
   pumping fluid out of the fluid chamber with an electrically actuated pump.

2. A method as claimed in claim 1, further comprising the step of:
   implanting the movable wall member, pump housing and electrically actuated pump into a patient's body.

3. A method as claimed in claim 1, wherein
   at least a portion of the wall member is resilient.

4. A method as claimed in claim 1, wherein
   at least a portion of the wall member is a bellows.

5. A method as claimed in claim 1, wherein
   the step of biasing a movable wall member comprises self-biasing a movable wall member away from the pump housing with enough force to create a pressure within the fluid chamber that is negative with respect to the ambient pressure.

6. A method as claimed in claim 1, wherein
   the step of biasing a movable wall member comprises biasing a movable wall member away from the pump housing with a spring with enough force to create a pressure within the fluid chamber that is negative with respect to the ambient pressure.

7. A method as claimed in claim 1, further comprising the step of:
   drawing fluid through a needle and into the fluid chamber with the pressure that is negative with respect to the ambient pressure.

8. A method, comprising the step of:
   biasing a movable wall member, which is carried by a pump housing and has a first side that defines a fluid chamber and a second side that is exposed to ambient pressure, away from the pump housing with enough force to create a pressure within the fluid chamber that is negative with respect to the ambient pressure; and
   storing medication in the fluid chamber.

9. A method as claimed in claim 8, further comprising the step of:
   pumping the medication out of the fluid chamber with a pump which is not the movable wall member that defines the fluid chamber.

10. A method as claimed in claim 8, further comprising the step of:
    implanting the movable wall member and pump housing into a patient's body.

11. A method as claimed in claim 8, wherein
    at least a portion of the wall member is resilient.

12. A method as claimed in claim 8, wherein
    at least a portion of the wall member is a bellows.

13. A method as claimed in claim 8, wherein
    the step of biasing a movable wall member comprises self-biasing a movable wall member away from the pump housing with enough force to create a pressure within the fluid chamber that is negative with respect to the ambient pressure.

14. A method as claimed in claim 8, wherein
    the step of biasing a movable wall member comprises biasing a movable wall member away from the pump housing with a spring with enough force to create a pressure within the fluid chamber that is negative with respect to the ambient pressure.

15. A method as claimed in claim 8, further comprising the step of:

drawing fluid through a needle and into the fluid chamber with the pressure that is negative with respect to the ambient pressure.

\* \* \* \* \*